US009775998B2

(12) United States Patent
Fredelake (10) Patent No.: US 9,775,998 B2
(45) Date of Patent: Oct. 3, 2017

(54) SYSTEMS AND METHODS FOR DETECTING DEGRADATION OF A MICROPHONE INCLUDED IN AN AUDITORY PROSTHESIS SYSTEM (71) Applicant: ADVANCED BIONICS AG, Staefa (CH)

(72) Inventor: Stefan Fredelake, Hannover (DE)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/907,272

(22) PCT Filed: Jul. 23, 2013

(86) PCT No.: PCT/IB2013/056041
§ 371 (c)(1),
(2) Date: Jan. 22, 2016

(87) PCT Pub. No.: WO2015/011525
PCT Pub. Date: Jan. 29, 2015

(65) Prior Publication Data
US 2016/0158546 A1 Jun. 9, 2016

(51) Int. Cl.
*H04B 15/00* (2006.01)
*A61N 1/36* (2006.01)
(Continued)

(52) U.S. Cl.
CPC ........ *A61N 1/36032* (2013.01); *G10L 21/038* (2013.01); *G10L 25/60* (2013.01);
(Continued)

(58) Field of Classification Search
CPC ..... G10L 15/22; G10L 21/0232; G10L 25/78; G10L 15/02; H04R 3/04; H04R 1/22; H04R 2225/43; H04R 2460/13
(Continued)

(56) References Cited

U.S. PATENT DOCUMENTS 5,844,994 A * 12/1998 Graumann ........... H04R 29/004
348/E7.083
8,223,982 B2 7/2012 Ibrahim
(Continued)

FOREIGN PATENT DOCUMENTS

EP 0989775 3/2000
EP 2257034 12/2010

OTHER PUBLICATIONS

International Search Report and Written Opinion received in International Application No. PCT/IB13/056041, dated Feb. 11, 2014.
(Continued)

*Primary Examiner* — Alexander Jamal
(74) *Attorney, Agent, or Firm* — ALG Intellectual Property, LLC (57) ABSTRACT An exemplary system includes a sound processor associated with a patient and a microphone (102). The microphone is configured to detect an audio signal presented to the patient and output an output signal (302) representative of the audio signal. The sound processor is configured to 1) receive the output signal, 2) identify at least one temporal portion of the output signal that has a classification attribute associated with a reference signal, 3) determine (304) a signal characteristic value (306) associated with the at least one temporal portion, 4) determine (308) that a difference (312) between the signal characteristic value associated with the at least one temporal portion and a reference signal characteristic value (310) associated with the reference signal meets a threshold condition, the meeting of the threshold condition indicating that a quality level of the microphone is below an acceptable level and 5) perform a predetermined action associated with the quality level of the microphone.

20 Claims, 7 Drawing Sheets (51) Int. Cl.
   *H04R 25/00*   (2006.01)
   *G10L 21/038*  (2013.01)
   *G10L 25/60*   (2013.01)
   *G10L 25/78*   (2013.01)
   *G10L 25/51*   (2013.01)

(52) U.S. Cl.
   CPC ............ *G10L 25/78* (2013.01); *H04R 25/305* (2013.01); *G10L 25/51* (2013.01)

(58) Field of Classification Search
   USPC ..... 381/312, 320, 321, 94.2, 94.7, 101, 102, 381/103, 94.9; 704/231, 233
   See application file for complete search history.

(56) References Cited

U.S. PATENT DOCUMENTS

| | | | |
|---|---|---|---|
| 2004/0181266 A1 | 9/2004 | Wakefield | |
| 2005/0259829 A1* | 11/2005 | Van den Heuvel | H04R 25/30 381/60 |
| 2007/0118011 A1 | 5/2007 | Harrison | |
| 2008/0249771 A1* | 10/2008 | Wahab | G10L 25/78 704/233 |
| 2009/0185704 A1* | 7/2009 | Hockley | G10L 17/26 381/316 |
| 2010/0189292 A1 | 7/2010 | Wurzbacher et al. | |
| 2010/0208631 A1 | 8/2010 | Zhang et al. | |
| 2010/0274554 A1* | 10/2010 | Orr | G10L 25/78 704/201 |
| 2011/0213444 A1 | 9/2011 | Stoffaneller et al. | |
| 2013/0085549 A1* | 4/2013 | Case | H04R 25/305 607/55 |

OTHER PUBLICATIONS

Advanced Bionics, "Neida CI Listening Check", http://www.advancedbionics.com/com/en/products/accessories/listeningcheck.html as accessed Apr. 1, 2014.

Advanced Bionics, "Advanced Bionics Harmony Listening Check."

* cited by examiner

SYSTEMS AND METHODS FOR DETECTING DEGRADATION OF A MICROPHONE INCLUDED IN AN AUDITORY PROSTHESIS SYSTEM

BACKGROUND INFORMATION

Various types of auditory prosthesis systems have been developed to assist patients who have severe (e.g., complete) hearing loss. For example, cochlear implant systems may provide a sense of hearing for sensorineural hearing loss patients by providing electrical stimulation representative of sound directly to stimulation sites within the cochlea. As another example, electro-acoustic stimulation ("EAS") systems may assist patients with some degree of residual hearing in the low frequencies (e.g., below 1000 Hz) by providing acoustic stimulation representative of low frequency audio content and electrical stimulation representative of high frequency content.

Many auditory prosthesis systems include a sound processor apparatus (e.g., a behind-the-ear ("BTE") sound processing unit, a body worn device, etc.) configured to be located external to the patient. The sound processor apparatus may perform a variety of functions, such as processing audio signals presented to the patient, controlling an operation one or more implantable devices (e.g., one or more cochlear implants), and providing power to the one or more implantable devices.

Audio signals presented to the patient are initially detected by a microphone located near the ear of the patient, such as mounted to an ear hook coupled to a housing that houses the sound processor. In order to properly detect sound, at least a portion of the microphone typically must be exposed to the environment. As a result, the microphone is exposed to many environmental contaminants such as skin, earwax, perspiration, and the like. The environmental contaminants and ordinary wear due to continued operation may cause the microphone to degrade. Degradation may manifest itself as a general decrease in sensitivity (e.g., drift) as well as a change in the frequency response of the microphone.

For small children especially, this degradation can be difficult to detect. Where the degradation affects the intelligibility of speech, the learning and language development of children can be affected. For patients in general, the degradation may occur slowly over time and therefore not be perceptible.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for detecting degradation of a microphone included in an auditory prosthesis system are described herein. An exemplary system includes a sound processor associated with a patient and configured to maintain data representative of a reference signal characteristic value and a classification attribute both associated with a reference signal. The system may further include a microphone communicatively coupled to the sound processor and configured to detect an audio signal presented to the patient and output an output signal representative of the audio signal.

In some examples, the sound processor may receive the output signal output by the microphone, identify at least one temporal portion of the output signal that has the classification attribute associated with the reference signal, determine a signal characteristic value associated with the at least one temporal portion, and determine that a difference between the signal characteristic value associated with the at least one temporal portion and the reference signal characteristic value associated with the reference signal meets a threshold condition. As will be described below, a meeting of the threshold condition may indicate that a quality level of the microphone is below an acceptable level. In response to a determination that the difference between the signal characteristic value associated with the at least one temporal portion and the reference signal characteristic value associated with the reference signal meets the threshold condition, the sound processor may perform a predetermined action associated with the quality level of the microphone.

In one exemplary implementation, the predetermined action includes adjusting one or more control parameters that govern an operation of the auditory prosthesis system (i.e., the sound processor and/or a cochlear implant implanted within the patient). In another exemplary implementation, the predetermined action includes providing a notification that the quality level of the microphone is below the acceptable level (e.g., by providing an alert by way of a light emitting device, a speaker, etc.).

As used herein, a "signal characteristic value" refers to a value that indicates or describes (e.g., quantifies) a particular characteristic of a signal (or a portion of a signal, such as a temporal portion of an output signal as identified by a sound processor). For example, a signal characteristic value may indicate an amount of spectral energy included in a signal, describe a spectral shape of a signal, specify a sound pressure level of a signal, and/or otherwise describe any other characteristic of a signal as may serve a particular implementation. A "reference signal characteristic value" may similarly refer to a value that indicates or describes (e.g., quantifies) a particular characteristic of a reference signal used by a sound processor to evaluate a quality level of a microphone.

As used herein, a "classification attribute" refers to any suitable attribute that may be used to classify a signal (or a portion of a signal, such as a temporal portion of an output signal as identified by a sound processor) as being of a particular type. For example, a particular signal may have one or more classification attributes that indicate that the signal includes speech, music, or noise.

As an example of the systems and methods described herein, it may be desirable to monitor a quality level of a microphone included in an auditory prosthesis system (e.g., a microphone, such as a "T-Mic", that is configured to be placed within the concha of the ear near the entrance to the ear canal). To this end, the sound processor may maintain data representative of a long term average speech spectrum (which, in this example, is the reference signal characteristic value) that represents an average spectral energy profile in at least a portion of the audible frequency range for speech (which, in this example, is the classification attribute). The sound processor may continuously monitor an output signal of the microphone and identify at least one temporal portion of the output signal that includes speech. The sound processor may then compare a spectral energy of the at least one temporal portion with the long term average speech spectrum and determine that a difference between the two meets a threshold condition (e.g., that the spectral energy is not within an acceptable tolerance range of the long term average speech spectrum for a predetermined amount of time (e.g., two to three days)). In response, the sound processor may determine that the quality level of the microphone is below an acceptable level (i.e., that the microphone has degraded in quality) and adjust one or more control parameters that govern an operation of the auditory prosthesis system (e.g., by increasing a gain applied to the output signals generated by the microphone), provide a notification that the quality level of the microphone is below the acceptable level (e.g., by providing an alert by way of a light emitting device, a speaker, etc.), and/or perform any other suitable predetermined action as may serve a particular implementation.

By continuously monitoring specific temporal portions of the output of a microphone, such as portions corresponding to speech, relative to data associated with a reference signal and maintained by a sound processor, the systems and methods described herein may advantageously facilitate real-time evaluation of a quality level of a microphone, regardless of variability in the audio signals detected by the microphone. This is because the signal characteristics of the temporal portions identified, particularly the spectral energy of speech, are relatively constant if a quality level of the microphone is at or above an acceptable level.

Figure 1:
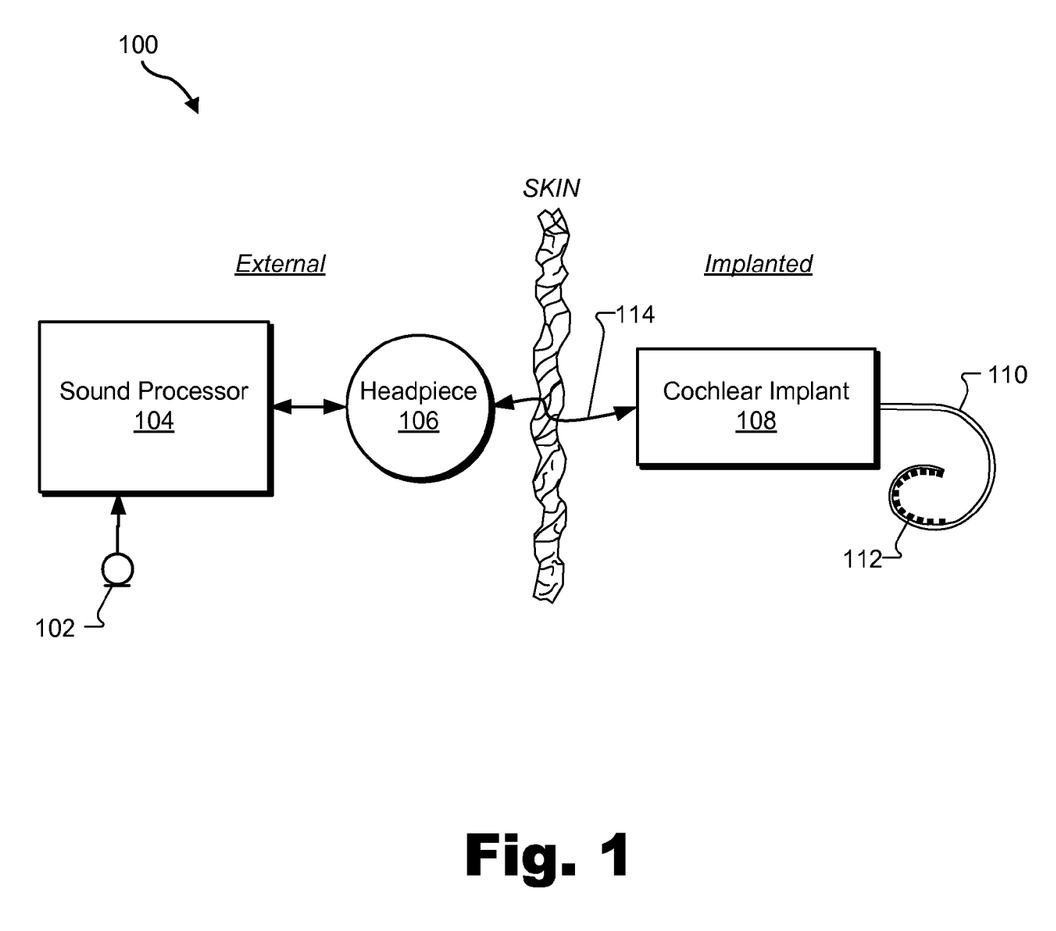
FIG. 1 illustrates an exemplary auditory prosthesis system according to principles described herein.

FIG. 1 illustrates an exemplary auditory prosthesis system 100 that may be configured to detect and/or compensate for degradation of a microphone. Auditory prosthesis system 100 may include a microphone 102, a sound processor 104, a headpiece 106 having a coil disposed therein, a cochlear implant 108, and a lead 110 with a plurality of electrodes 112 disposed thereon. Additional or alternative components may be included within auditory prosthesis system 100 as may serve a particular implementation.

As shown, auditory prosthesis system 100 may include various components configured to be located external to a patient including, but not limited to, microphone 102, sound processor 104, and headpiece 106. Auditory prosthesis system 100 may further include various components configured to be implanted within the patient including, but not limited to, cochlear implant 108 and lead 110.

Microphone 102 may be configured to detect audio signals presented to the patient and output output signals representative of the audio signals for processing by sound processor 104. Microphone 102 may be implemented in any suitable manner. For example, microphone 102 may include a "T-Mic" or the like that is configured to be placed within the concha of the ear near the entrance to the ear canal. Such a microphone may be held within the concha of the ear near the entrance of the ear canal by a boom or stalk that is attached to an ear hook configured to be selectively attached to sound processor 104 (i.e., to a housing that houses sound processor 104). Additionally or alternatively, microphone 102 may be implemented by a microphone disposed within headpiece 106, a microphone disposed within a housing that houses sound processor 104, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 114 between headpiece 106 and cochlear implant 108. It will be understood that communication link 114 may include a bi-directional communication link and/or one or more dedicated uni-directional communication links.

As will be described in more detail below, sound processor 104 may determine or evaluate (e.g., continuously monitor) a quality level of microphone 102. Sound processor 104 may perform any suitable predetermined action associated with the quality level of microphone 102 based on the determination. Exemplary predetermined actions that may be performed by sound processor 104 will be described in more detail below.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may be additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 114 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the patient via one or more electrodes 112 disposed along lead 110. In some examples, cochlear implant 108 may include a plurality of independent current sources each associated with a channel defined by one or more of electrodes 112. In this manner, different stimulation current levels may be applied to multiple stimulation sites simultaneously by way of multiple electrodes 112.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

Figure 2:
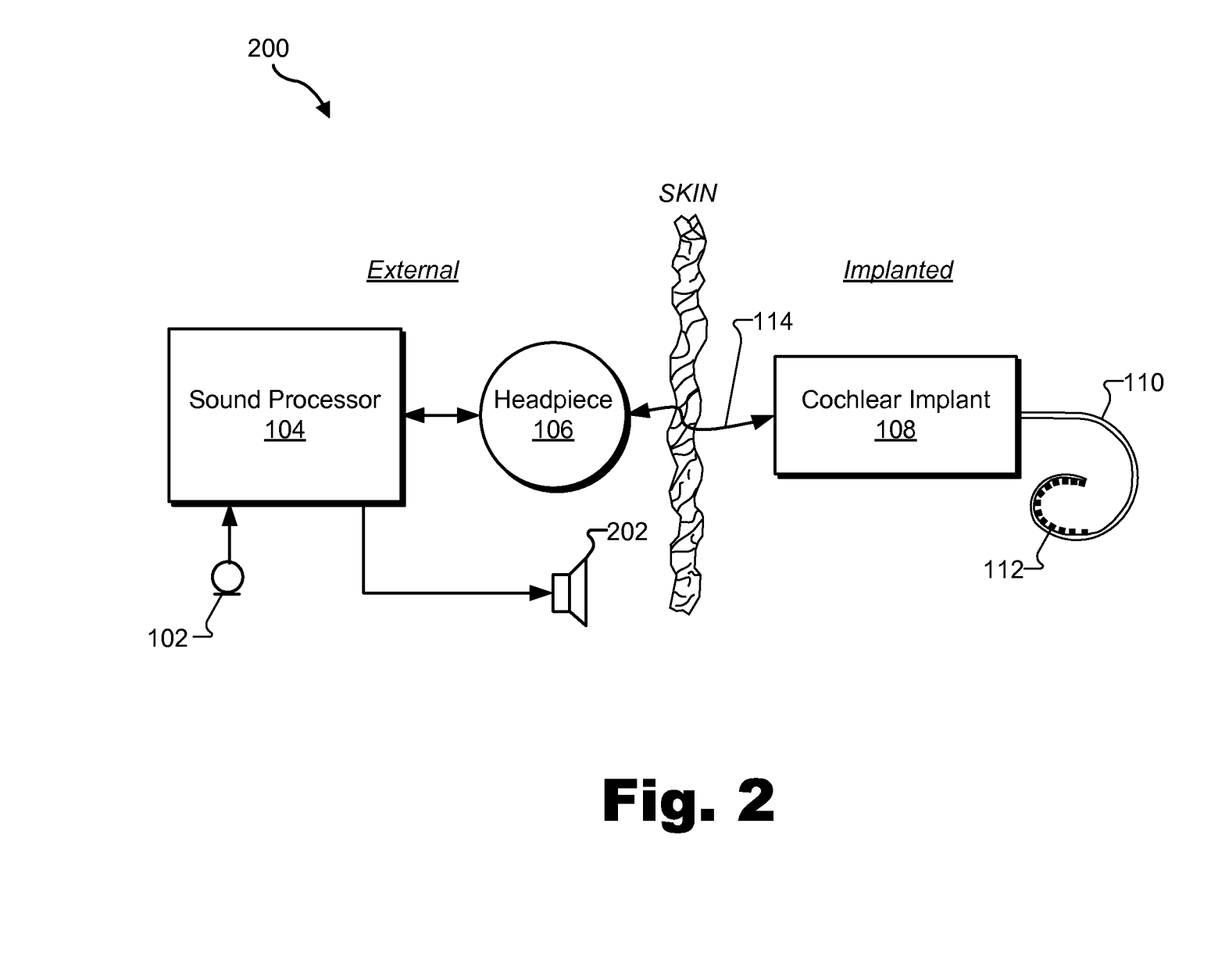
FIG. 2 illustrates another exemplary implementation of the auditory prosthesis system of FIG. 1 according to principles described herein.

FIG. 2 illustrates an exemplary implementation 200 of auditory prosthesis system 100 in which auditory prosthesis system 100 is further configured to provide acoustic stimulation to the patient. Hence, implementation 200 shown in FIG. 2 may be referred to as an electro-acoustic stimulation ("EAS") system.

As shown, implementation 200 may further include a receiver 202 (also referred to as a loudspeaker). In this configuration, sound processor 104 may be configured to direct receiver 202 to apply acoustic stimulation representative of audio content included in a relatively low frequency band (e.g., below 1000 Hz) to the patient and cochlear implant 108 to apply electrical stimulation representative of audio content included in a relatively high frequency band (e.g., above 1000 Hz) to one or more stimulation sites within the patient by way of one or more of electrodes 112.

As mentioned, sound processor 104 may evaluate a quality level of microphone 102. To this end, sound processor 104 may maintain data representative of a reference signal characteristic value and a classification attribute both associated with a reference signal. As described above, the reference signal characteristic value indicates or describes (e.g., quantifies) a particular characteristic of a reference signal to which a signal characteristic value of one or more temporal portions of an output signal of microphone 102 may be compared. The classification attribute indicates that the reference signal is (or includes) a particular type of signal (e.g., speech, music, or noise).

In some examples, sound processor 104 may receive an output signal output by microphone 102 and representative of an audio signal detected by microphone 102. Sound processor 104 may identify at least one temporal portion of the output signal that has the same classification attribute as the reference signal. For example, if the classification attribute of the reference signal is associated with speech (i.e., if the reference signal is representative of speech), sound processor 104 may identify one or more temporal portions of the output signal that are also associated with speech. This may be performed in any suitable manner. For example, sound processor 104 may identify the at least one temporal portion of the output signal that has the classification attribute by identifying at least one characteristic (e.g., at least one temporal characteristic) of the output signal that corresponds to the classification attribute. Examples of this will be provided below.

Once at least one temporal portion of the output signal has been identified as having the same classification attribute as the reference signal, sound processor 104 may determine a signal characteristic value associated with the at least one temporal portion of the output signal. This may be performed in any suitable manner. For example, sound processor 104 may identify a plurality of temporal portions of the output signal as having the same classification attribute as the reference signal. In response, sound processor 104 may determine a signal characteristic value associated with the plurality of temporal portions by determining a plurality of signal characteristic values associated with the plurality of temporal portions and averaging the plurality of signal characteristic values to obtain an averaged signal characteristic value. The averaged signal characteristic value may then be designated by sound processor 104 as the signal characteristic value associated with the at least one temporal portion of the output signal.

Once the signal characteristic value associated with the at least one temporal portion of the output signal has been determined, sound processor 104 may compare the signal characteristic value with the reference signal characteristic value.

If sound processor 104 determines that the difference between the signal characteristic value associated with the at least one temporal portion of the output signal and the reference signal characteristic value does not meet a threshold condition (e.g., if the difference is less than a predetermined threshold), sound processor 104 may determine that a quality level of microphone 102 is at or above an acceptable level. In contrast, if sound processor 104 determines that the difference between the signal characteristic value associated with the at least one temporal portion of the output signal and the reference signal characteristic value does meet the threshold condition (e.g., if the difference is greater than a predetermined threshold), sound processor 104 may determine that the quality level of microphone 102 is below the acceptable level. In response, sound processor 104 may perform one or more predetermined actions associated with the quality level of the microphone. Exemplary predetermined actions that may be performed by sound processor 104 will be described in more detail below.

Figure 3:
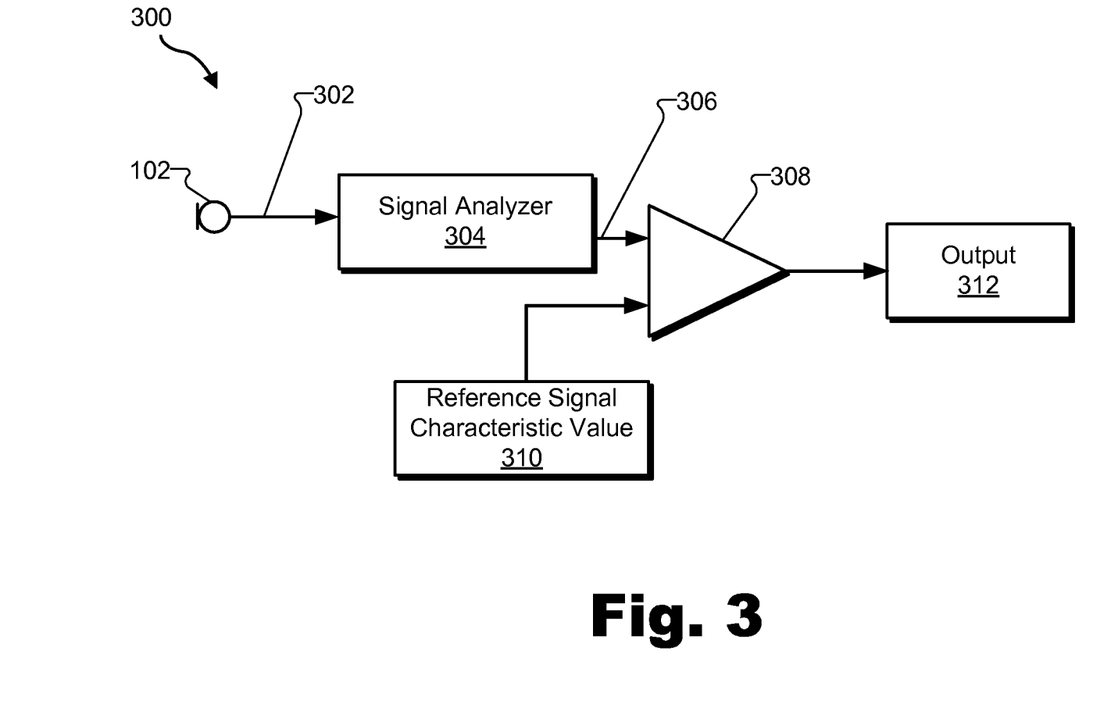
FIG. 3 illustrates an exemplary signal processing scheme that may be used by a sound processor according to principles described herein.

FIG. 3 illustrates an exemplary signal processing scheme 300 that may be used by sound processor 104 to perform some or all of operations described herein. The illustrated components in FIG. 3 may be actual circuits included in sound processor 104 or representative of one or more software modules executed within sound processor 104.

As shown, microphone 102 may produce an output signal (represented by arrow 302) representative of an audio signal presented to a cochlear implant patient. The output signal may be received by a signal analyzer 304, which may analyze the output signal by identifying at least one temporal portion of the output signal that has the same classification attribute as the classification attribute maintained by sound processor 104 (i.e., the classification attribute of the reference signal). Signal analyzer 304 may identify the at least one temporal portion of the output signal that has the classification attribute by identifying at least one characteristic of the output signal that corresponds to the classification attribute.

To illustrate, the classification attribute maintained by sound processor 104 may be associated with speech, thereby indicating that the reference signal contains speech. In this example, signal analyzer 304 may identify the at least one temporal portion of the output signal that has the classification attribute by identifying at least one characteristic of the output signal that corresponds to speech. Such characteristics include, but are not limited to, modulation frequency, onset flank, offset flank, occurrence of one or more voiced segments, occurrence of one or more unvoiced segments, pitch, and/or other characteristics of speech. For example, signal analyzer 304 may determine that a particular temporal portion of the output signal has a modulation frequency that is typically associated with speech. Signal analyzer 304 may accordingly identify the temporal portion as being associated with speech.

Signal analyzer 304 may be further configured to determine a signal characteristic value for the at least one temporal portion of output signal 302. This may be performed in any suitable manner. For example, in some embodiments, the signal characteristic value associated with the at least one temporal portion may be obtained by identifying a plurality of temporal portions (e.g., over a period of time, such as a few days), determining a plurality of signal characteristic values associated with the plurality of temporal portions, and averaging the plurality of signal characteristic values to obtain an averaged signal characteristic value. The averaged signal characteristic value may then be designated as the signal characteristic value associated with the plurality of temporal portions.

For example, signal analyzer 304 may receive an output signal from microphone 102 during a particular time window (e.g., N days) and identify a plurality of temporal portions of the output signal that have a classification attribute that matches a classification attribute maintained by sound processor 104. The time window may be a sliding window, e.g., temporal portions identified within N days from a current time point may be used to continuously or periodically evaluate the quality of the microphone 102 according to the systems and methods described herein. Signal analyzer 304 may determine a plurality of signal characteristic values associated with the plurality of temporal portions and then average the signal characteristic values. The averaged signal characteristic value may then be used as the signal characteristic value that is subsequently compared to a reference signal characteristic value maintained by sound processor 104.

Signal analyzer 304 may output data representative of a signal characteristic value (represented by arrow 306). As shown, the output may be input to a comparator 308. Comparator 308 may compare the signal characteristic value with a reference signal characteristic value 310 associated with a reference signal and maintained (e.g., stored) by sound processor 104. For example, comparator 308 may determine a difference between the signal characteristic value and the reference signal characteristic value 310 (e.g., by subtracting one value from another, determining a ratio of one value to another, etc.). Data representative of the difference may be output as output 312.

Reference signal characteristic value 310 may be associated with any suitable reference signal as may serve a particular implementation. For example, reference signal characteristic value 310 may be associated with a reference signal that is general (i.e., used for many auditory prosthesis patients) or specific to a particular auditory prosthesis patient. In one exemplary implementation, the reference signal characteristic value 310 is an established reference such as a long term average speech spectrum (i.e., a value that represents an average spectral energy profile in at least a portion of the audible frequency range for speech). In another exemplary implementation, the reference signal characteristic value 310 is a long term speech spectrum specific to the patient. For example, for a period after the auditory prosthesis system 100 is fitted to the patient, temporal portions of an output signal output by microphone 102 may be identified as described above and the spectral energy profiles of these signals may be computed and averaged. This average spectral energy profile may then be used as the reference signal characteristic value 310 for subsequent evaluations of the quality of microphone 102.

Additionally or alternatively, reference signal characteristic value 310 may include a spectral shape value representative of a spectral shape of the reference signal. In these embodiments, signal analyzer 304 may determine a signal characteristic value of one or more temporal portions of the output signal produced by microphone 102 by determining a spectral shape value of the one or more temporal portions. The spectral shape value may be determined measuring a spectral gravity value of the one or more temporal portions, a kurtosis value of the one or more temporal portions, a skewness value of the one or more temporal portions, and/or any other attribute of the one or more temporal portions as may serve a particular implementation.

Additionally or alternatively, reference signal characteristic value 310 may include a sound pressure level associated with the reference signal. In these embodiments, signal analyzer 304 may determine a signal characteristic value of one or more temporal portions of the output signal produced by microphone 102 by measuring a sound pressure level of the one or more temporal portions. This may be performed in any suitable manner.

Comparator 308 may compare the signal characteristic value with a reference signal characteristic value 310 associated with a reference signal and maintained (e.g., stored) by sound processor 104. For example, comparator 308 may determine a difference between the signal characteristic value and the reference signal characteristic value 310. As mentioned, data representative of the difference between the signal characteristic value associated with the at least one temporal portion of the output signal produced by microphone 102 and the reference signal characteristic value 310 may be output by comparator 308 as output 312. In cases in which the signal characteristic value and the reference signal characteristic value 310 each include a plurality of values, the output 312 may include a plurality of difference values each representing a difference between a signal characteristic value and a corresponding reference signal characteristic value 310.

Sound processor 104 may be configured to evaluate output 312 with respect to a threshold condition. For example, the sound processor 104 may determine that output 312 meets or exceeds a threshold condition. For example, if the output 312 is greater than or equal to a threshold value, sound processor 104 may determine that the threshold condition is met (i.e., that the quality level of microphone 102 is below an acceptable level). Conversely, sound processor 104 may determine that the output 312 does not meet the threshold condition if output 312 is within an acceptable range of values. For example, if output 312 is less than the threshold value, sound processor 104 may determine that the threshold condition is not met (i.e., that the quality level of microphone 102 is at or above the acceptable level).

Where the output 312 includes a plurality of difference values, the sound processor 104 may evaluate each difference value with respect to a different threshold value to obtain a plurality of comparison values. Sound processor 104 may accordingly evaluate the quality of microphone 102 based on the plurality of comparison values (e.g., a weighted combination of the plurality of comparison values). Any heuristic may be used to determine whether the plurality of comparison values indicate that the quality level of microphone 102 is acceptable or unacceptable.

In some examples, sound processor 104 may maintain a plurality of classification attributes and a plurality of class-specific reference signal characteristic values each corresponding to a particular classification attribute included in the plurality of classification attributes. For example, sound processor 104 may maintain classification attributes corresponding to speech in quiet, speech with noise, music, and/or any other type of audio signal. In this manner, microphone 102 may be evaluated by sound processor 104 for various types of audio signals presented to the patient.

Figure 4:
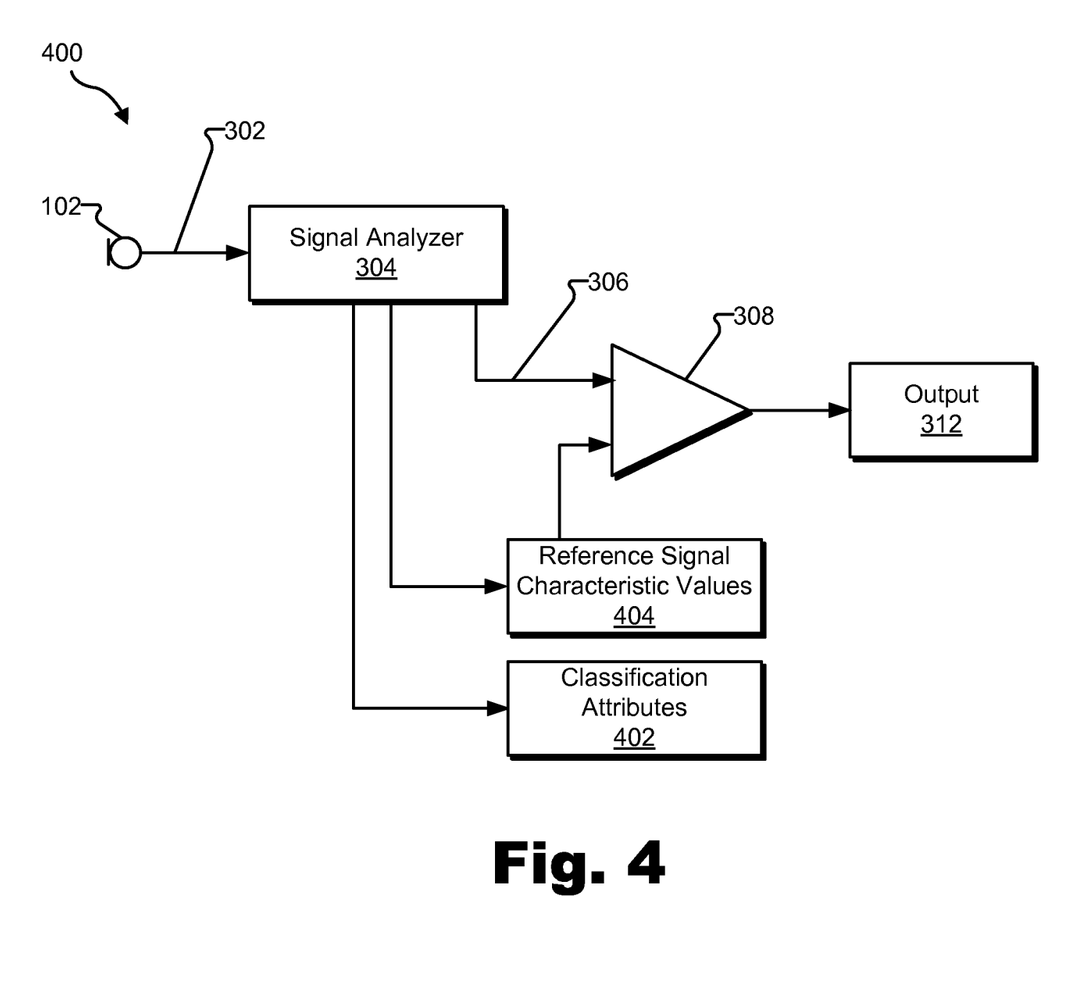
FIG. 4 illustrates another exemplary signal processing scheme that may be used by a sound processor according to principles described herein.

To illustrate, FIG. 4 illustrates another exemplary signal processing scheme 400 that may be used by sound processor 104 to determine whether a quality level of microphone 102 has degraded below an acceptable level. Signal processing scheme 400 is similar to signal processing scheme 300, except that the signal analyzer 304 maintains data representative of a plurality of classification attributes 404 (e.g., speech in quiet, speech in noise, music, and/or any other classification attribute as may serve a particular implementation) and data representative of a plurality of class-specific reference signal characteristic values 404. Each class-specific reference signal characteristic value included in class-specific reference signal characteristic values 404 corresponds to a classification attribute included in the plurality of classification attributes 402.

As shown, signal analyzer 304 may have access to classification attributes 402 and reference signal characteristic values 404. In this configuration, signal analyzer 304 may classify one or more temporal portions of output signal 302 as having a particular classification attribute included in classification attributes 402 maintained by sound processor 104. This may be performed in any suitable manner. For example, signal analyzer 304 may identify one or more characteristics (e.g., one or more temporal characteristics) of a temporal portion of output signal 302 and, based on the one or more characteristics, determine that the temporal portion has a particular classification attribute included in classification attributes 402.

Once a classification attribute for a temporal portion of output signal 302 has been identified, signal analyzer 304 may select a class-specific reference signal characteristic value corresponding to the classification attribute from the plurality of class-specific reference signal characteristic values 404 and use the selected class-specific reference value in the comparison performed by comparator 308. This comparison may be performed in a manner similar to that described in connection with FIG. 3.

Sound processor 104 may perform a variety of different predetermined actions in response to a determination that the output 312 meets a threshold condition (i.e., in response to a determination that a quality level of microphone 102 is below an acceptable level).

For example, the predetermined action may include sound processor 104 adjusting one or more control parameters that govern an operation of auditory prosthesis 100 (e.g., sound processor 104 and/or cochlear implant 108). To illustrate, microphone 102 may decrease in sensitivity, thereby causing output 312 to increase accordingly. In response, sound processor 104 may increase a gain applied to the output of microphone 102 proportionally. As another example, a change in output 312 may indicate a change in the frequency response of microphone 102. In response, sound processor 104 may adjust the spectral profile of a processed version of the output of the microphone 102 based on output 312.

The predetermined action may additionally or alternatively include sound processor 104 providing a notification that the quality level of microphone 102 is below the acceptable level. In this manner, a user (e.g., the patient, a clinician, etc.) may be made aware of the degraded microphone 102 and take one or more actions to address the quality level of microphone 102 (e.g., by cleaning, replacing, adjusting, and/or otherwise doing something to microphone 102 to increase the quality level of microphone 102).

Figure 5:
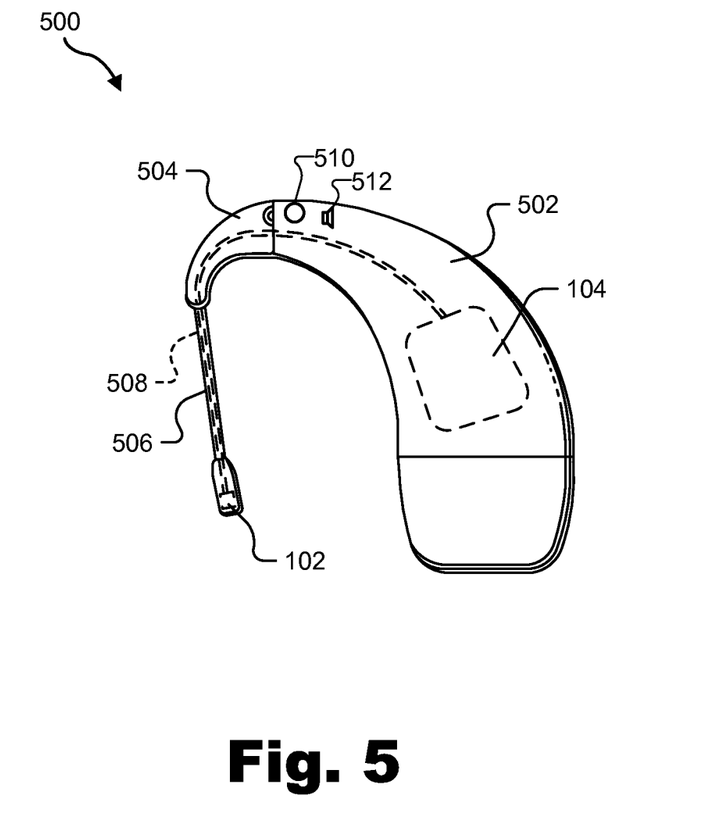
FIG. 5 illustrates another exemplary implementation of the auditory prosthesis system of FIG. 1 according to principles described herein.

Sound processor 104 may provide a notification that the quality level of microphone 102 is below the acceptable level in any suitable manner. For example, FIG. 5 illustrates an exemplary implementation 500 of auditory prosthesis system 100. Implementation 500 may include a housing 502 (e.g., a behind the ear (BTE) housing) configured to be worn behind the ear of the patient and an ear hook assembly 504 configured to connect to housing 502. In some examples, sound processor 104 is entirely disposed within housing 502. Microphone 102 may be located near the opening of the ear canal. For example, as shown, microphone 102 may be coupled to ear hook assembly 504 by way of a stalk 506 (also referred to as a boom). Stalk 506 may be made from a bendable material that retains its bent position, thereby allowing the microphone assembly to be positioned, through selective bending of stalk 506, at a desired location near the opening of the ear canal. In some examples, microphone 102 may be communicatively coupled to sound processor 104 by way of a communication link 508 (e.g., one or more wires).

The illustrated implementation 500 may include one or both of a light emitting diode ("LED") 510 and a speaker 512 integrated into housing 502. The LED 510 and speaker 512 may be communicatively coupled to sound processor 104. It will be recognized that implementation 500 may alternatively not include LED 510 or speaker 512.

In some examples, sound processor 104 may provide the notification by way of LED 510 (or any other suitable light emitting device) and/or speaker 512. For example, sound processor 104 may provide the notification by activating LED 510 (e.g., by causing LED 510 to blink or remain illuminated).

Additionally or alternatively, sound processor 104 may provide the notification by activating speaker 512 (e.g., by causing speaker 512 to generate an audible alert). In some examples in which it is desirable to notify only the patient of the degradation in microphone 102, sound processor 104 may provide the notification by activating receiver 202 shown in FIG. 2.

In some examples, sound processor 104 may provide the notification by producing a diagnostic signal at a diagnostic interface (e.g., a fitting device, a computing device, or the like) communicatively coupled to sound processor 104. The diagnostic interface may then provide the notification (e.g., by way of a graphical user interface) based on the diagnostic signal.

Sound processor 104 may additionally or alternatively provide the notification by directing cochlear implant 108 to provide the notification to the patient. For example, sound processor 104 may direct cochlear implant 108 to excite one or more electrodes 112 in a manner that causes the patient to perceive a recognizable signal, such as a buzzing or beeping sound, voice message, or other signal.

It will be recognized that the light emitting devices, speakers, diagnostic interfaces, and cochlear implants are all illustrative of output devices that may be coupled to sound processor 104 and configured to generate a perceptible output indicating a degradation of microphone 102. Other output devices may additionally or alternatively be used to notify one or more users of the degradation of microphone 102 as may serve a particular implementation.

In some examples, different threshold conditions may be used to determine whether sound processor 104 adjusts one or more parameters governing an operation of auditory prosthesis system 100 or provides a notification indicative of a degradation in quality of microphone 102. For example, if a first threshold condition is met according to any of the implementations described herein, sound processor 104 may adjust one or more parameters governing an operation of auditory prosthesis system 100. However, if the degradation of microphone 102 is more extensive (e.g., of a second more stringent threshold condition is met), sound processor 104 may provide the notification.

Figure 6:
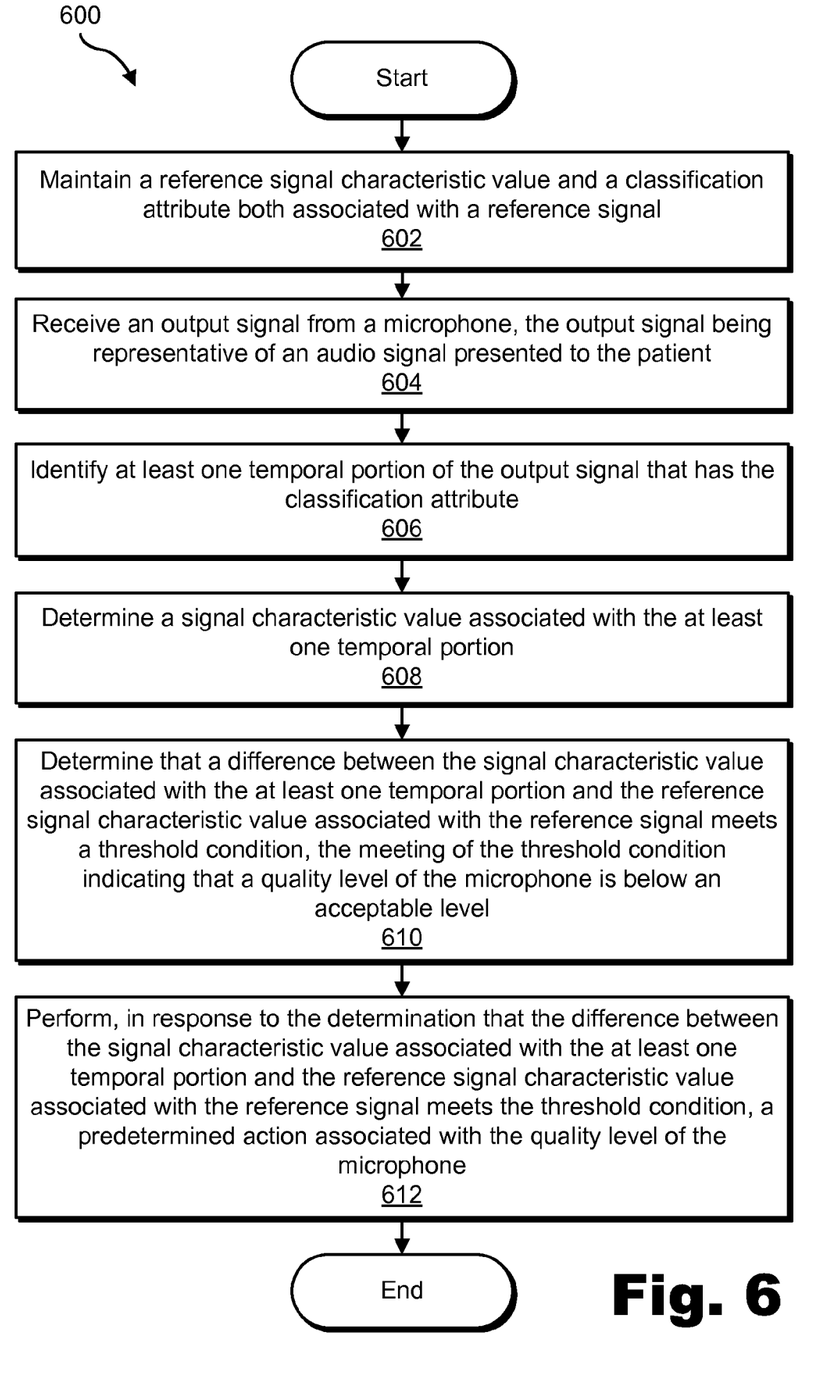
FIG. 6 illustrates an exemplary method of detecting degradation of a microphone included in an auditory prosthesis system according to principles described herein.

FIG. 6 illustrates an exemplary method of detecting degradation of a microphone included in an auditory prosthesis system. While FIG. 6 illustrates exemplary steps according to one exemplary implementation, other implementations may omit, add to, reorder, and/or modify any of the steps shown in FIG. 6. One or more of the steps shown in FIG. 6 may be performed by sound processor 104 and/or any implementation thereof.

In step 602, a sound processor maintains a reference signal characteristic value and a classification attribute that are both associated with a reference signal. Step 602 may be performed in any of the ways described herein.

In step 604, the sound processor receives an output signal from a microphone. The output signal may be representative of an audio signal presented to the patient. Step 604 may be performed in any of the ways described herein.

In step 606, the sound processor identifies at least one temporal portion of the output signal that has the classification attribute. Step 606 may be performed in any of the ways described herein.

In step 608, the sound processor determines a signal characteristic value associated with the at least one temporal portion identified in step 606. Step 608 may be performed in any of the ways described herein.

In step 610, the sound processor determines that a difference between the signal characteristic value associated with the at least one temporal portion and the reference signal characteristic value associated with the reference signal meets a threshold condition. As described above, this may indicate that a quality level of the microphone is below an acceptable level. Step 610 may be performed in any of the ways described herein.

In step 612, the sound processor performs, in response to the determination made in step 610, a predetermined action associated with the quality level of the microphone. Step 612 may be performed in any of the ways described herein.

Figure 7:
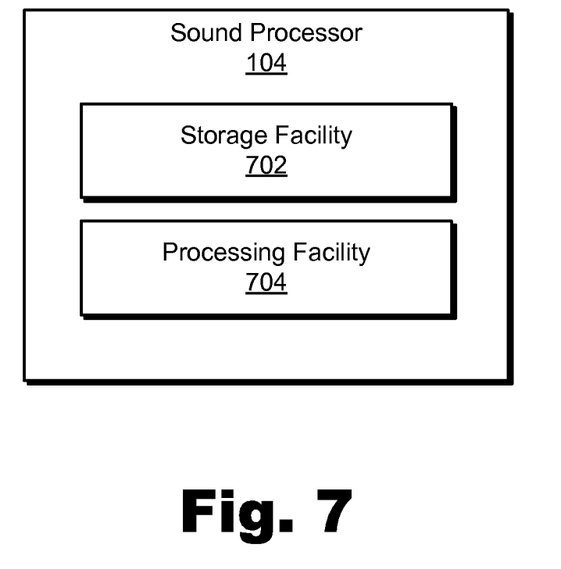
FIG. 7 illustrates exemplary components of a sound processor according to principles described herein.

FIG. 7 illustrates exemplary components of sound processor 104. As shown in FIG. 7, sound processor 104 may include a storage facility 702 and a processing facility 704, which may be communicatively coupled to one another using any suitable communication technologies. Each of these facilities will now be described in more detail.

Storage facility 702 may be configured to maintain data representative of one or more reference signal characteristic values and one or more classification attributes associated with a reference signal. Storage facility 702 may maintain any other data as may serve a particular implementation.

Processing facility 704 may be configured to perform one or more of the processing operations described herein. To this end, processing facility 704 may be implemented by one or more computing devices (e.g., signal processing devices).

Various other implementations for detecting degradation of a microphone may also be used alone or in combination with the implementations described hereinabove. For example, inasmuch as degradation of a microphone may be at least partially in response to moisture, oils, earwax, or other substances to which the microphone is exposed, a sensor may be included within auditory prosthesis system 100 (e.g., on the surface of microphone 102) and configured to provide a notification (e.g., by changing color) in response to sensing some or all of these above-listed substances. Accordingly, likely degradation of the microphone 102 may be inferred from the notification provided by the sensor.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system for detecting microphone degradation in an auditory prosthesis system, the system comprising:
   a sound processor associated with a patient and configured to maintain data representative of a reference signal characteristic value and a classification attribute both associated with a reference signal; and
   a microphone communicatively coupled to the sound processor and configured to detect an audio signal presented to the patient and output an output signal representative of the audio signal;
   wherein the sound processor is further configured to
      receive the output signal for a predetermined amount of time that is greater than one day,
      identify at least one temporal portion of the output signal that has the classification attribute,
      determine a signal characteristic value associated with the at least one temporal portion,
      determine that a difference between the signal characteristic value associated with the at least one temporal portion and the reference signal characteristic value associated with the reference signal meets a threshold condition for the predetermined amount of time that is greater than one day, the meeting of the threshold condition for the predetermined amount of time that is greater than one day indicating that a quality level of the microphone is below an acceptable level, and perform, in response to the determination that the difference between the signal characteristic value associated with the at least one temporal portion and the reference signal characteristic value associated with the reference signal meets the threshold condition for the predetermined amount of time that is greater than one day, a predetermined action associated with the quality level of the microphone.

2. The system of claim 1, wherein the classification attribute identifies the at least one temporal portion as including speech.

3. The system of claim 1, wherein the sound processor is configured to identify the at least one temporal portion of the output signal that has the classification attribute by identifying at least one characteristic of the output signal that corresponds to the classification attribute.

4. The system of claim 3, wherein:
the classification attribute is associated with speech; and
the at least one characteristic includes at least one of a modulation frequency, an onset flank, an offset flank, an occurrence of a voiced segment, and an occurrence of an unvoiced segment.

5. The system of claim 1, wherein the sound processor is configured to:
identify the at least one temporal portion of the output signal that has the classification attribute by identifying a plurality of temporal portions of the output signal that have the classification attribute; and
determine the signal characteristic value by
determining a plurality of signal characteristic values associated with the plurality of temporal portions, and
averaging the plurality of signal characteristic values to obtain an averaged signal characteristic value.

6. The system of claim 1, wherein the signal characteristic value comprises a spectral energy of the at least one temporal portion and the reference signal characteristic value comprises a spectral energy of the reference signal.

7. The system of claim 1, wherein the signal characteristic value comprises a spectral shape value of the at least one temporal portion and the reference signal characteristic value comprises a spectral shape value of the reference signal.

8. The system of claim 7, wherein the sound processor is configured to determine the spectral shape value of the at least one temporal portion by measuring at least one of a spectral gravity value of the at least one temporal portion, a kurtosis value of the at least one temporal portion, and a skewness value of the at least one temporal portion.

9. The system of claim 1, wherein the signal characteristic value comprises a sound pressure level of the at least one temporal portion and the reference signal characteristic value comprises a sound pressure level of the reference signal.

10. The system of claim 1, wherein the sound processor is configured to:
maintain data representative of the classification attribute by maintaining a plurality of classification attributes including the classification attribute as one of the plurality of classification attributes; and
identify the at least one temporal portion of the output signal that has the classification attribute by classifying the at least one temporal portion as corresponding to the classification attribute from among the plurality of classification attributes.

11. The system of claim 10, wherein the plurality of classification attributes each correspond to one of speech in quiet, speech with noise, and music.

12. The system of claim 10, wherein the sound processor is configured to:
maintain data representative of the reference signal characteristic value by maintaining a plurality of class-specific reference signal characteristic values each corresponding to one of the plurality of classification attributes, the plurality of class-specific reference signal characteristic values including the reference signal characteristic value; and
determine that the difference between the signal characteristic value associated with the at least one temporal portion and the reference signal characteristic value associated with the reference signal meets the threshold condition by:
selecting the reference signal characteristic value from among the plurality of class-specific reference signal characteristic values based on the classifying of the temporal portion as corresponding to the classification attribute, and
determining that a difference between the selected reference signal characteristic value and the signal characteristic value meets the threshold condition.

13. The system of claim 1, wherein the sound processor is configured to perform the predetermined action associated with the quality level of the microphone by adjusting one or more control parameters that govern an operation of at least one of the sound processor and a cochlear implant implanted within the patient.

14. The system of claim 1, wherein the sound processor is configured to perform the predetermined action associated with the quality level of the microphone by providing a notification that the quality level of the microphone is below the acceptable level.

15. The system of claim 14, wherein the sound processor is configured to provide the notification by activating at least one of:
a light-emitting device communicatively coupled to the sound processor.
a speaker communicatively coupled to the sound processor; and
a diagnostic interface communicatively coupled to the sound processor.

16. A system for detecting microphone degradation in an auditory prosthesis system, the method comprising:
a storage facility configured to maintain data representative of a reference signal characteristic value and a classification attribute associated with a reference signal; and
a processing facility communicatively coupled to the storage facility and configured to
receive, for a predetermined amount of time that is greater than one day, an output signal representative of an audio signal as detected by a microphone,
identify at least one temporal portion of the output signal that has the classification attribute,
determine a signal characteristic value associated with the at least one temporal portion,
determine that a difference between the signal characteristic value associated with the at least one temporal portion and the reference signal characteristic associated with the reference signal meets a threshold condition for the predetermined amount of time that is greater than one day, the meeting of the threshold condition for the predetermined amount of time that is greater than one day indicating that a quality level of the microphone is below an acceptable level, and perform, in response to the determination that the difference between the signal characteristic value associated with the at least one temporal portion and the reference signal characteristic value associated with the reference signal meets the threshold condition for the predetermined amount of time that is greater than one day, a predetermined action associated with the quality level of the microphone.

17. The system of claim 16, wherein the classification attribute identifies the at least one temporal portion as including speech.

18. The system of claim 16, wherein the storage facility is configured to maintain data representative of the classification attribute by maintaining a plurality of classification attributes including the classification attribute as one of the plurality of classification attributes; and wherein the processing facility is configured to identify the at least one temporal portion of the output signal that has the classification attribute by classifying the at least one temporal portion as corresponding to the classification attribute from among the plurality of classification attributes.

19. The system of claim 18, wherein the storage facility is configured to maintain data representative of the reference signal characteristic value by maintaining a plurality of class-specific reference signal characteristic values, each corresponding to one of the plurality of classification attributes, the plurality of class-specific reference signal characteristic values including the reference signal characteristic value; and wherein the processing facility is configured to determine that the difference between the signal characteristic value associated with the at least one temporal portion and the reference signal characteristic value associated with the reference signal meets the threshold condition by:

selecting the reference signal characteristic value from among the plurality of class-specific reference signal characteristic values based on the classifying of the temporal portion as corresponding to the classification attribute; and determining that a difference between the selected reference value and the signal characteristic value meets the threshold condition.

20. A method for detecting microphone degradation in an auditory prosthesis system, the method comprising:

maintaining, by a sound processor associated with a patient, a reference signal characteristic value and a classification attribute both associated with a reference signal;

receiving, by the sound processor, an output signal from a microphone for a predetermined amount of time that is greater than one day, the output signal being representative of an audio signal presented to the patient;

identifying, by the sound processor, at least one temporal portion of the output signal that has the classification attribute;

determining, by the sound processor, a signal characteristic value associated with the at least one temporal portion; and determining, by the sound processor, that a difference between the signal characteristic value associated with the at least one temporal portion and the reference signal characteristic value associated with the reference signal meets a threshold condition for the predetermined amount of time that is greater than one day, meeting of the threshold condition for the predetermined amount of time that is greater than one day indicating that a quality level of the microphone is below an acceptable level; and performing, by the sound processor in response to the determination that the difference between the signal characteristic value associated with the at least one temporal portion and the reference signal characteristic value associated with the reference signal meets the threshold condition for the predetermined amount of time that is greater than one day, a predetermined action associated with the quality level of the microphone.

* * * * *